(12) United States Patent
Schon et al.

(10) Patent No.: US 8,795,165 B2
(45) Date of Patent: Aug. 5, 2014

(54) PIVOTING DILATOR

(75) Inventors: Donald Schon, Paradise Valley, AZ (US); Timothy Schweikert, Levittown, PA (US); John Stephens, Perkiomenville, PA (US)

(73) Assignees: Medical Components, Inc., Harleysville, PA (US); TwinCath, LLC, Paradise Valley, AZ (US)

( * ) Notice: Subject to any disclaimer, the term of this patent is extended or adjusted under 35 U.S.C. 154(b) by 1515 days.

(21) Appl. No.: 11/650,689

(22) Filed: Jan. 8, 2007

(65) Prior Publication Data

US 2007/0250100 A1     Oct. 25, 2007

Related U.S. Application Data

(60) Provisional application No. 60/757,225, filed on Jan. 9, 2006.

(51) Int. Cl.
    *A61B 17/02*        (2006.01)

(52) U.S. Cl.
    USPC ............... 600/219; 606/191; 600/184

(58) Field of Classification Search
    CPC ............... A61B 17/02; A61B 17/0206; A61B 17/0218; A61B 17/3439; A61B 1/32
    USPC ........ 606/108, 119, 192–199, 86 A, 86 B, 90, 606/104, 190, 191; 600/201–235, 184
    See application file for complete search history.

(56) References Cited

U.S. PATENT DOCUMENTS

| | | | |
|---|---|---|---|
| 281,880 A * | 7/1883 | Hubbell ..................... 600/219 |
| 673,598 A | 5/1901 | Dolge | |
| 1,358,473 A * | 11/1920 | Smith ......................... 600/225 |
| 2,456,257 A * | 12/1948 | Curry .......................... 604/106 |
| 2,842,133 A | 7/1958 | Uhma | |
| 3,893,454 A * | 7/1975 | Hagelin ....................... 600/219 |
| 4,010,740 A * | 3/1977 | Littorin ....................... 600/220 |
| 4,484,911 A | 11/1984 | Berlin et al. | |
| 4,889,112 A | 12/1989 | Schachner et al. | |
| 5,425,717 A | 6/1995 | Mohiuddin | |
| 5,667,473 A | 9/1997 | Finn et al. | |
| 5,785,648 A * | 7/1998 | Min .............................. 600/206 |
| 5,899,854 A * | 5/1999 | Slishman ..................... 600/219 |
| 6,004,341 A | 12/1999 | Zhu et al. | |
| 6,083,207 A | 7/2000 | Heck | |

(Continued)

OTHER PUBLICATIONS

International Search Report dated May 19, 2008, PCT Application No. PCT/US07/00196 (3 pages).

(Continued)

*Primary Examiner* — Kathleen Holwerda
(74) *Attorney, Agent, or Firm* — Glenn M. Massina, Esq.; Fox Rothschild LLP

(57) ABSTRACT

A dilator (100) for expanding a vessel incision to assist insertion of a catheter thereinto and having a distal end (104) and a proximal end (106). The dilator has two portions (110,210) that are assembled together at a hinge (112,212) permitting angled-apart proximal ends (122,222) of the two portions at the proximal end (106) to be squeezed together about the hinge which slightly spreads apart the respective distal ends (114,214) of the two portions to enlarge the incision into the vessel. A spring (150) biases apart the proximal ends of the two portions to maintain the two distal ends (114,214) together until pried apart as desired to dilate the vessel incision.

26 Claims, 8 Drawing Sheets

(56) References Cited

U.S. PATENT DOCUMENTS

| | | |
|---|---|---|
| 6,096,046 A * | 8/2000 | Weiss .......................... 606/119 |
| 6,361,541 B1 | 3/2002 | Barnhart |
| 6,425,901 B1 | 7/2002 | Zhu et al. |
| 6,623,460 B1 | 9/2003 | Heck |
| 6,796,991 B2 | 9/2004 | Nardeo |
| 6,849,064 B2 * | 2/2005 | Hamada .................. 604/164.01 |
| 6,896,680 B2 * | 5/2005 | Michelson ...................... 606/90 |
| 6,936,061 B2 | 8/2005 | Sasaki |
| 2002/0128659 A1 * | 9/2002 | Michelson ...................... 606/90 |
| 2004/0087975 A1 | 5/2004 | Lucatero et al. |
| 2004/0093001 A1 * | 5/2004 | Hamada ........................ 606/190 |
| 2005/0234507 A1 | 10/2005 | Geske et al. |

OTHER PUBLICATIONS

Written Opinion dated May 19, 2008; PCT Application No. PCT/US07/00196 (4 pages).

* cited by examiner

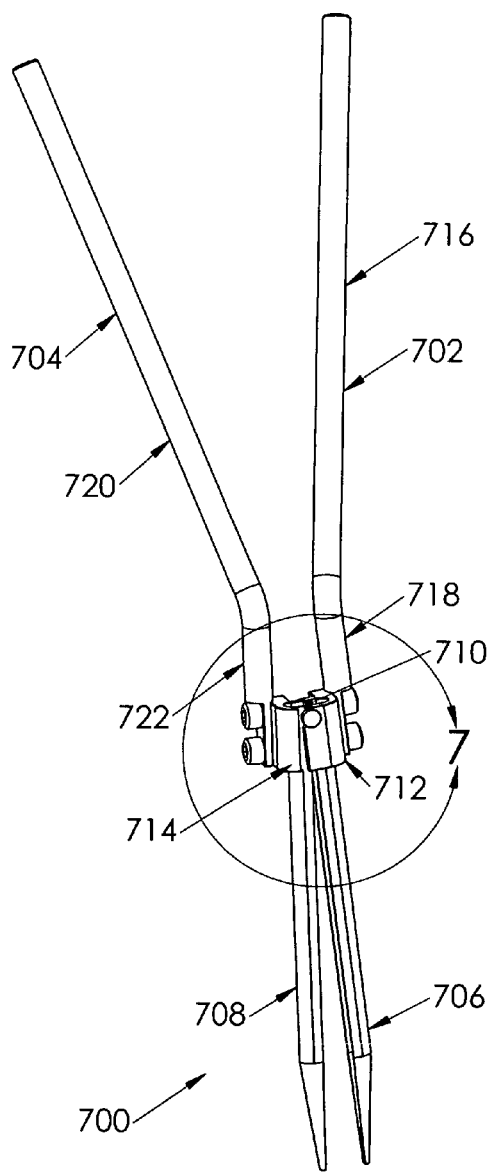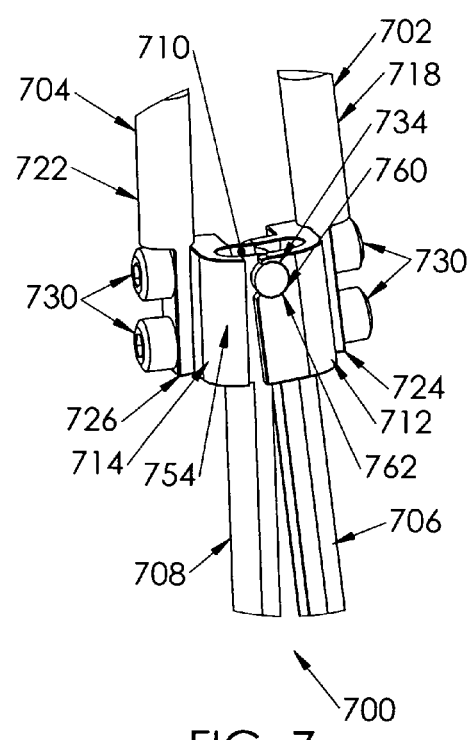
FIG. 6
FIG. 7

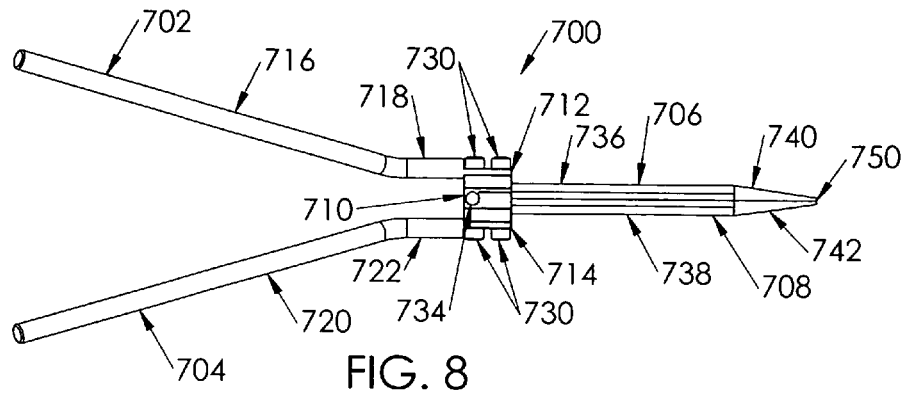
FIG. 8
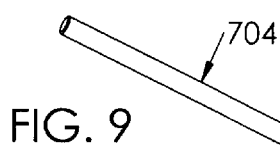
FIG. 9
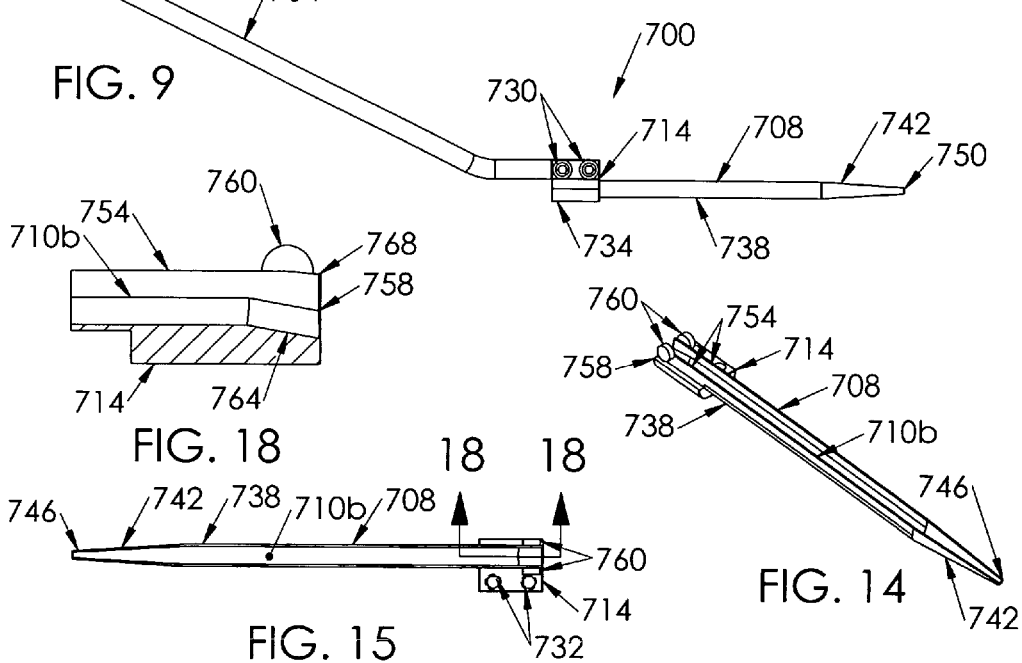
FIG. 18
FIG. 14
FIG. 15
FIG. 16
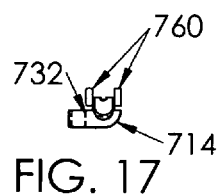
FIG. 17

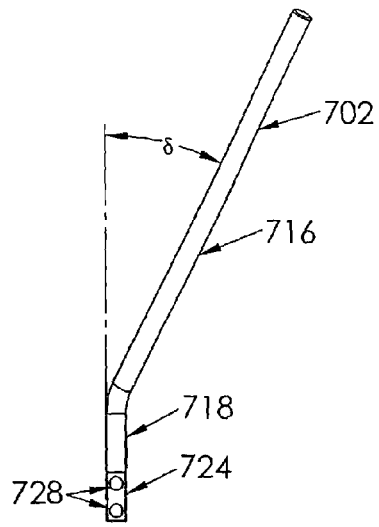
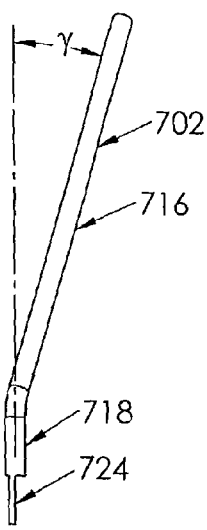
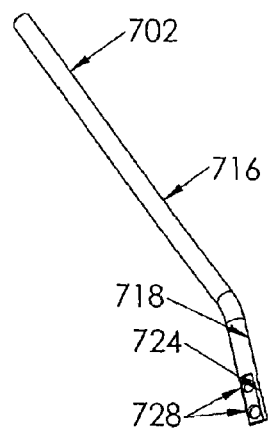
FIG. 12   FIG. 11   FIG. 10
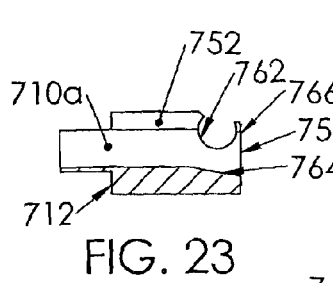
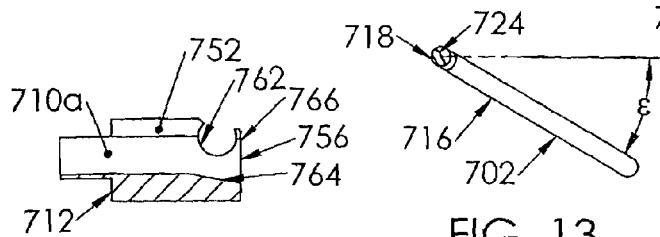
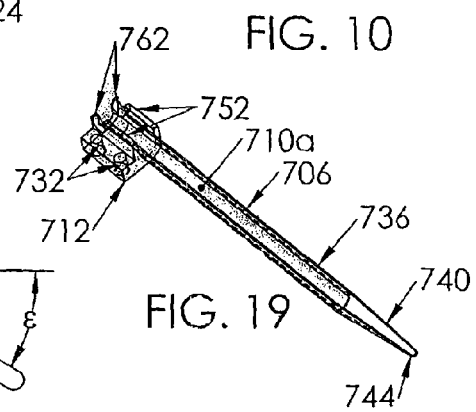
FIG. 23   FIG. 13   FIG. 19
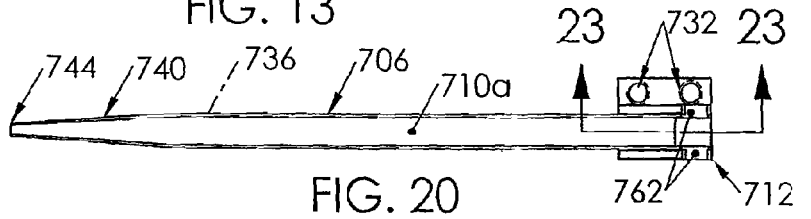
FIG. 20
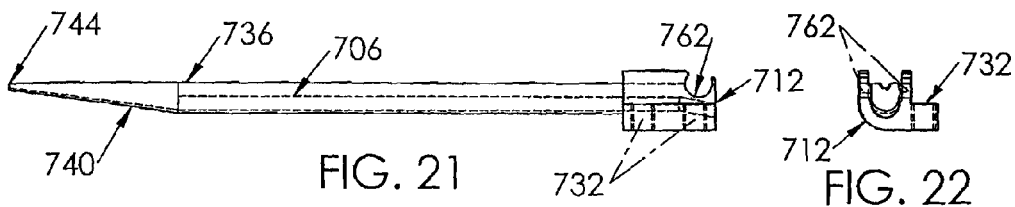
FIG. 21   FIG. 22

PIVOTING DILATOR

CROSS-REFERENCE TO RELATED APPLICATIONS

This application claims priority from U.S. Provisional Patent Application Ser. No. 60/757,225 filed Jan. 9, 2006.

FIELD OF THE INVENTION

The present invention relates to the field of medical devices and more particularly to vessel dilators.

BACKGROUND OF THE INVENTION

Catheters are used in numerous medical procedures. In particular, catheters are used for the introduction or removal of fluids from various venous and/or arterial regions and vessels throughout the body, such as for hemodialysis. The procedure by which these catheters are introduced to the body is delicate and complex. One particularly intricate challenge to catheterization is enlarging a hole in the flesh and vessel to be catheterized while minimizing blood loss and trauma to the patient.

Generally, to insert any catheter in a blood vessel, the vessel is identified by aspiration with a long hollow needle in accordance with the Seldinger technique. When blood enters a syringe attached to the needle, indicating that the vessel has been found, a thin guide wire is then introduced, typically through the syringe needle or other introducer device, into the interior of the vessel. The introducer device is then removed, leaving the guide wire within the vessel with a proximal end portion of the guide wire projecting beyond the surface of the skin.

At this point, several options are available to the practitioner for catheter placement. The simplest option is to pass a catheter into the vessel directly over the guide wire, whereafter the guide wire is removed; a variation on this option has been adopted recently in which a stylet is inserted about the guide wire within the catheter and which extends distally from the catheter's distal tip to facilitate entry of the catheter through the vessel incision, or venotomy. Both of these techniques require that the venotomy be predilated; even with predilation it is commonly difficult to insert the catheter through the venotomy, in certain patients, especially using the guide wire only.

If, however, the catheter is of a relatively large diameter and/or not made of a stiff material, one preferable method of inserting the catheter into the vessel is through an introducer sheath. The introducer sheath is simply a large, stiff thinwalled tube, which serves as a temporary conduit for the catheter that is being placed. Prior to use of the sheath, usually a plurality of smaller-to-larger size dilators are used in sequence, placed onto and removed from the guide wire, to attain the appropriately large size for the venotomy. The sheath is positioned by placing the final dilator to be used, which has a hollow passageway along its longitudinal axis, inside of the sheath and passing both the dilator and the sheath together into the vessel over the guide wire. The dilator expands the opening in the blood vessel to allow for catheter insertion into the vessel. The guide wire and dilator are then removed, leaving the thin-walled sheath in place. The catheter is then inserted through the sheath.

In a setting where a catheter with a hub or other attachment at the end of the catheter has a feature which is larger than that of the inner diameter of the sheath, it is necessary to have a tear-away sheath that can be split away from the catheter as the sheath is being removed from the patient. In the case where a sheath does not have a small diameter or a narrow point, the dilator is often used to aid in the insertion of the sheath. The dilator has a long tubular section, the outside diameter of which is slightly smaller than the inside diameter of the sheath. The dilator also has a point tip on its distal end and a hollow center, which runs along the entire length of the dilator. The dilator is inserted into the body with the guidewire running through its center, thereby allowing the tip of the dilator to follow the guidewire to the place that is to be catheterized. On its proximal end, the dilator may have a hub. Like the hub of the sheath, this hub can also serve a number of purposes, such as providing a stable handle to aid in guiding the dilator into the vein, and as a mechanism which can mate with the sheath hub to form a locked connection.

Some dilator and sheath assemblies that include a connection between the dilator and sheath are known. U.S. Pat. No. 6,796,991 discloses a sheath and dilator assembly in which the sheath hub and the dilator hub having mating female and male threads to establish a connection therebetween, with the dilator being removable after sheath tip access to the vasculature is attained, after which the catheter is then inserted over the guide wire and into and through the sheath into the vasculature.

Dilating devices are also known for use in dilating vasculature incisions for insertion thereinto of medical tubing into the vasculature such as a catheter or an intravenous tube. One such device is disclosed in U.S. Pat. No. 2,842,133 and has two embodiments each having first and second components that together define an elongate channel through which tubing is insertable. In one version, the first and second components are affixed to respective hinged transverse spring-loaded finger pieces, and their distal portions are pivotable apart against spring bias when the finger pieces are squeezed together, to part the distal ends of the two components and dilate the vein when the pair of pieces are manually squeezed together.

It is desired to provide a dilating device that is easily manipulated and operated by the practitioner, in a single step procedure, for catheter insertion.

SUMMARY OF THE INVENTION

The present invention, briefly, is a dilator assembly having first and second dilator portions, each having proximal and distal portions, a longitudinal axis extending between the first and second dilator portions, and a longitudinal passageway extending along the longitudinal axis between the distal portions. The first and second dilator portions are hingedly connected proximally of their distal portions, and the passageway is adapted to accommodate a catheter being inserted longitudinally therethrough. The pivoting dilator is operable between an insertable position and a dilating position by forcing the at least one of the first and second proximal ends toward the longitudinal axis and pivoting apart the first and second distal portions.

Preferably, the first and second distal end portions are frustoconical when together and have non-sharp distal tips, and no sharp exposed edges and corners. Also, the first and second proximal portions may be spring biased apart causing the first and second distal portions to be spring biased together;or, the first and second distal portions may be spring biased together distally of the hinge, causing the proximal portions to be biased apart. Preferably, also, the first and second proximal portions are ergonomically shaped handles for manual gripping and squeezing. The hinged connection between the first and second dilator portions may be located approximately midway along the longitudinal axis, and preferably is laterally offset to permit access to the longitudinal passageway for insertion of a catheter into and through the dilator.

The present invention provides the advantage of being easily manipulated and operated by the practitioner, in a single step procedure, for catheter insertion, having hand-grippable handles adapted to be held and operated manually by the practitioner. The dilating device of the present invention can replace the use of sequential dilators and introducer sheaths in a single step procedure that enables controlled venotomy dilation to only the desired size; and its use significantly reduces the potential of air embolism or blood leakage that would occur after removal of a dilator from a sheath just prior to insertion of the catheter into the sheath, in prior methods.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 6 is an isometric view of a fourth embodiment of dilator, an assembly having multiple components;

FIG. 7 is an enlarged isometric view of the hub connection of the dilator assembly of FIG. 6;

FIGS. 8 and 9 are top and side views of the dilator assembly of FIGS. 6 and 7;

FIGS. 10 to 13 are, respectively, an isometric, top, side and end view of one of the two proximal portions of the dilator assembly of FIGS. 6 to 9;

FIGS. 14 to 18 are isometric, top, side, end and enlarged hub views of one distal portion of the dilator assembly of FIGS. 6 to 9; and FIGS. 19 to 23 are isometric, top, side, end and enlarged hub views of the other distal portion of the dilator assembly of FIGS. 6 to 9.

DETAILED DESCRIPTION OF THE INVENTION

Figure 1:
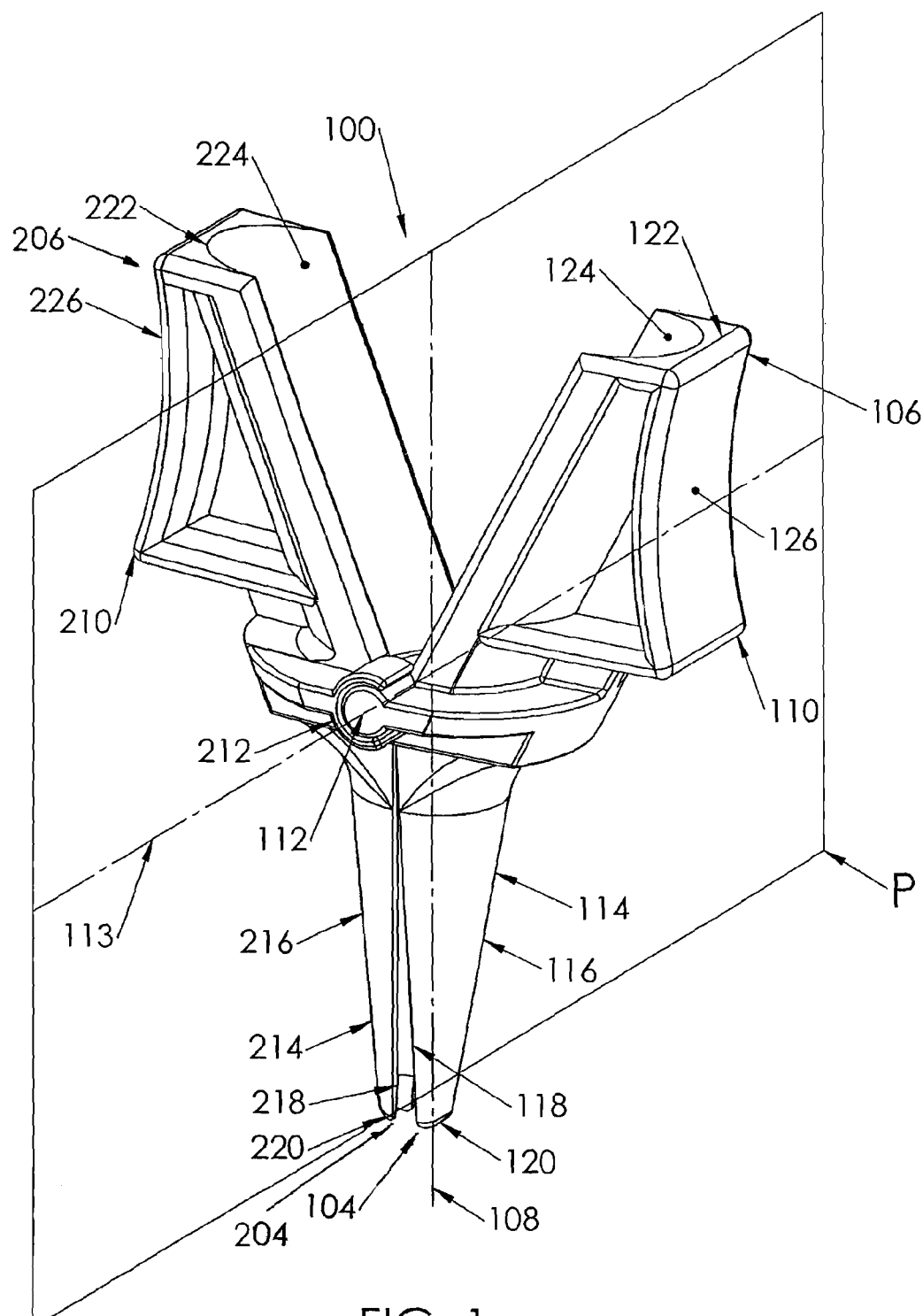
FIG. 1 is an isometric view of a pivoting dilator, according to a first embodiment of the present invention.

In the drawings, like numerals indicate like elements throughout. The words "proximal" and "distal" refer to directions away from and closer to, respectively, the insertion tip of a dilator according to the present invention. The terminology includes the words above specifically mentioned, derivatives thereof, and words of similar import. The following describes a preferred embodiments of the invention. However, it should be understood based on this disclosure, that the invention is not limited by the preferred embodiment described herein.

Referring to FIG. 1, a vessel dilator 100 according to the present invention is disclosed. The dilator 100 is used to expand an incision into a vessel to assist a physician during insertion of a catheter (not shown) into a patient's blood vessel (not shown) usually over a guide wire (not shown) extending through the dilator. The dilator 100 includes a distal end 104 that is to be inserted into the blood vessel through an incision or venotomy, and also includes a proximal end 106 that remains outside of the blood vessel when the distal end 104 of the dilator 100 is inserted into the blood vessel. A longitudinal axis 108 extends through the dilator 100 between the distal end 104 and the proximal end 106.

A first dilator portion 10 extends between the distal end 104 and the proximal end 106 generally on one side of a plane P which encompasses the longitudinal axis 108. A second dilator portion 210 extends between the distal end 104 and the proximal end 106 generally on an opposing side of the plane P from the first dilator portion 110. The first dilator portion 110 includes a male hinge portion 112 disposed between the distal end 104 and the proximal end 106. The second dilator portion 210 includes a female hinge portion 212, adapted to mate to the male hinge portion 112 and also disposed between the second distal end 204 and the second proximal end 206.

Figure 2:
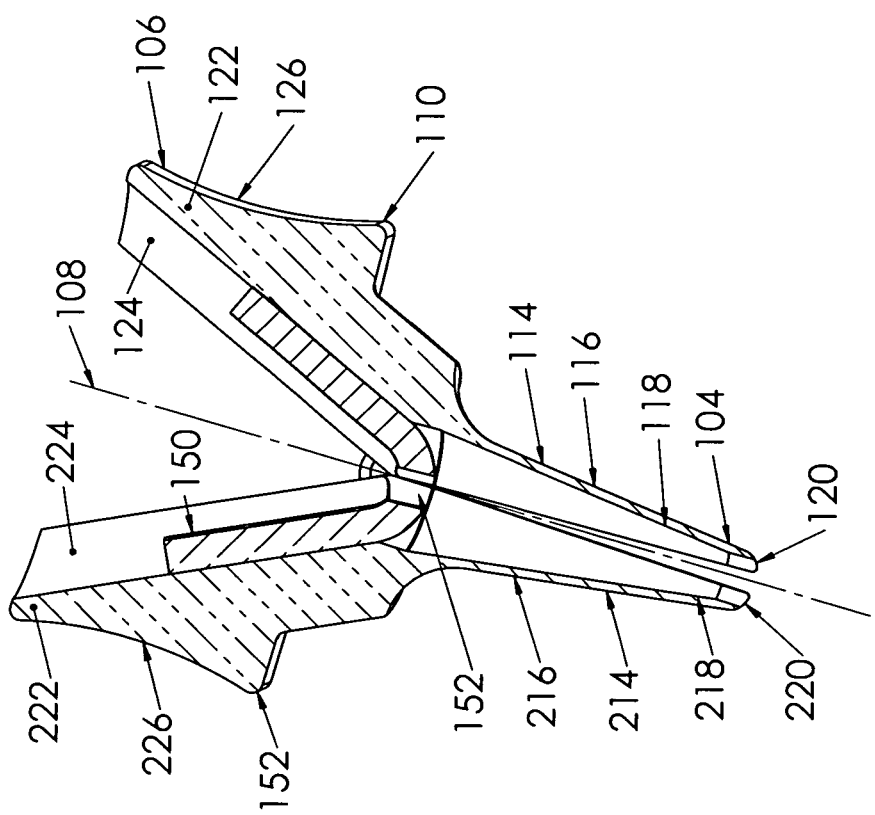
FIG. 2 is an isometric view of the pivoting dilator shown in FIG. 1 opened to illustrate the inside surfaces.

Referring now to FIGS. 1 and 2, the first dilator portion 110 has a first distal portion 114 concluding in a first distal tip 120 and having a first distal outer surface 116 and a first distal inner surface 118. The second dilator portion 210 has a second distal portion 214 concluding in a second distal tip 220 and is defined by a second distal outer surface 216 and a second distal inner surface 218. The first and second distal portions 114,214 have a generally C-shaped cross-section, when the cross-sectional view is taken in a plane that is perpendicular to the longitudinal axis 108, and together define a passageway through the first and second distal portions. The hinge portions 112, 212 connect the proximal ends of the first and second distal portions 110, 210 upon assembly and maintain them adjacent each other thereafter.

The first dilator portion 110 has a first proximal portion 122 having a first inner surface 124 that is generally semicircular and concave, and has a second dilator portion 210 has a second proximal portion 222 that has a second inner surface 224 that is generally semicircular and concave. Preferably, the semicircular and concave shape of the first and second inner surfaces 124,224 is an extension of the C-shaped cross section of the first and second distal portions 114,214, thereby giving the first and second inner surfaces 124,224 a generally C-shaped cross section, and together define a passageway through the first and second proximal portions when the first and second proximal portions 122,222 are pivoted together that aligns with the passageway through the first and second distal portions.

Both the first and second distal portions 114,214 are tapered away from the proximal portions 112,212, respectively, decreasing in width and thickness moving closer to their respective distal tips 120,220 distally along the longitudinal axis 108 from the proximal end 106.

With the exception of the male hinge portion 112 and the female hinge portion 212, preferably the first dilator portion 110 and the second dilator portion 210 are generally mirror images of each other. Those skilled in the art will recognize that the first and the second dilator portion 110,210 may have either the male hinge portion 112 or the female hinge portion 212.

Preferably, the male hinge portion 112 has a generally circular profile and extends from a point on the first dilator portion 110 that is located between the first distal portion 114 and the first proximal portion 122. The male hinge portion 112 is disposed about a hinge axis 113 extending therethrough that is located within the plane P and is perpendicular with the longitudinal axis 108. Preferably, the male hinge portion 112 comprises two portions that are disposed one on either side of the C-shaped cross section of the first inner surface 124, so that there is an unobstructed passageway extending between the proximal end 106 and the distal end 104 along the first proximal inner surface 124 and the first distal inner surface 118. The female hinge portion 212 is generally C-shaped complementary to the generally circular profile of the male hinge portion 112, and disposed along the second dilator portion 210 between the second proximal portion 222 and the second distal portion 214. The open end of the generally C-shaped female hinge portion 212 faces the first dilator portion 110.

Preferably, the female hinge portion 212 is sized to hingedly engage the male hinge portion 112 when the male hinge portion 112 is inserted inside of the open end of the female hinge portion 212. When the dilator is assembled, the female hinge portion 212, like the male hinge portion 112, is disposed about the hinge axis 113. Preferably, the female hinge portion 212 comprises two portions disposed one on either side of the C-shaped cross section of the second inner surface 224 at the same points along the hinge axis 113 as the male hinge portion 112, so that there is an unobstructed passageway extending between the proximal end 106 and the distal end 104 along the second proximal inner surface 224 and the second distal inner surface 218.

Figure 4:
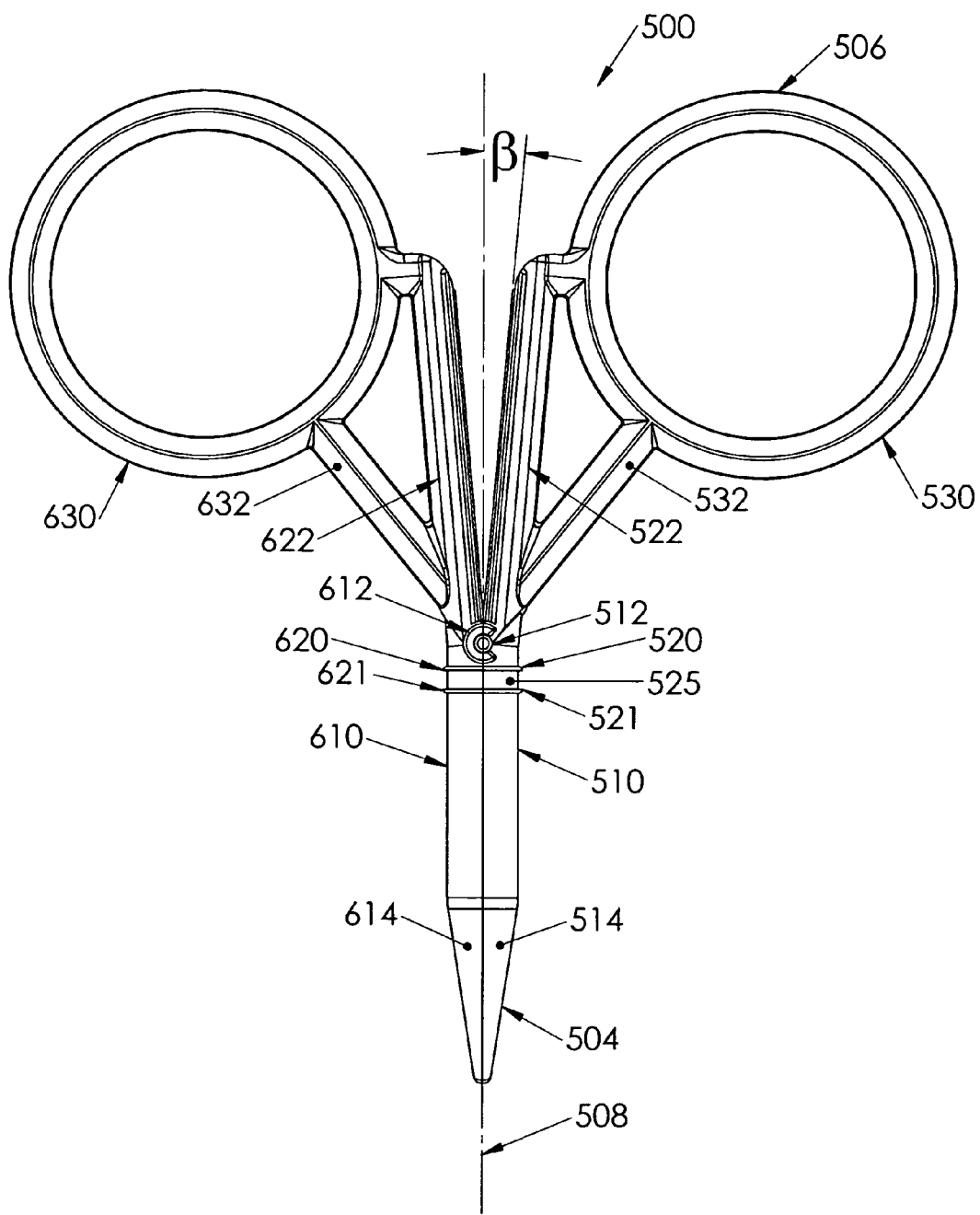
FIG. 4 is a side view of a third embodiment of the pivoting dilator.
Figure 5:
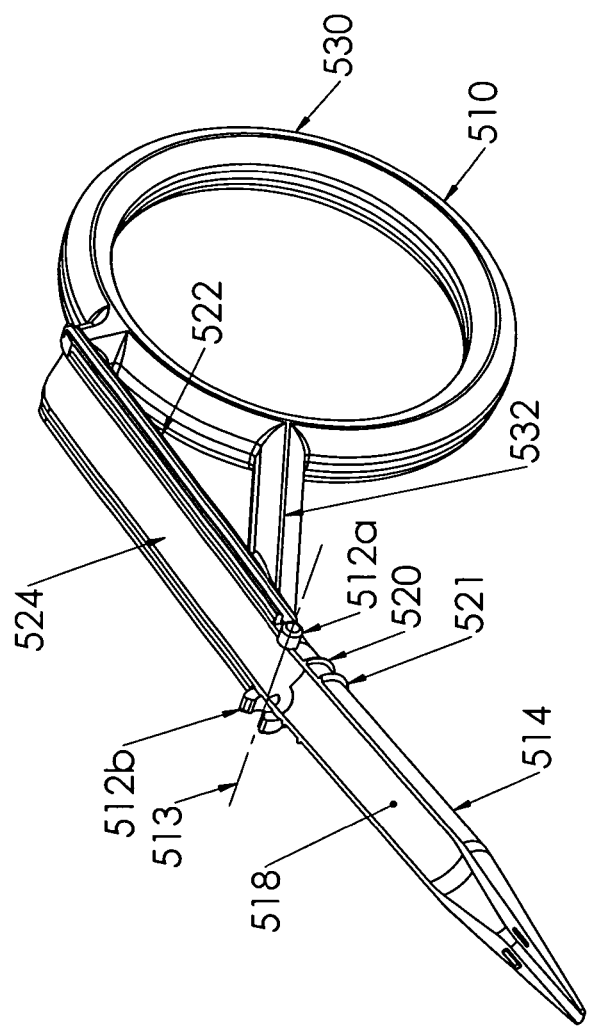
FIG. 5 is an isometric view of one of the two identical halves of the pivoting dilator in FIG. 4.

Preferably, when the male hinge portion 112 is engaged with the female hinge portion 212, the female hinge portion 212 is partially rotatable about both the male hinge portion 112 and the hinge axis 113. While the current embodiment shows the male hinge portion 112 is disposed on the first dilator portion 110 and the female hinge portion 212 is disposed on the second dilator portion 210, those skilled in the art will recognize that there are other hinge configurations that may be used to achieve the same result of hingedly connecting the first dilator portion 110 to the second dilator portion 210 without departing from the scope of the present invention. An example of such an alternate embodiment as shown in FIGS. 4 and 5, is a dilator 100 wherein the first dilator portion 110 may have one male hinge portion 112 and one female hinge portion 212, and correspondingly, the second dilator portion 210 may also have one male hinge portion 112 and one female hinge portion 212. This type of optional configuration for the dilator portions 110,210 provides for two identical dilator portions to be hingedly mated together to form the dilator 100, thereby reducing production costs. In assembly, the mating male and female hinge portions 112, 212 of the first and second dilator portions 110,210 may be mated together to hingedly connect the first dilator portion 110 to the second dilator portion 210.

As shown in FIG. 1, when the assembled dilator 100 is in an insertable position, the first and second distal ends 114,214 are disposed towards each other and the first and second proximal portions 122,222 are angled away from the plane P. The portions of the first and second proximal portions 122, 222 that are closest to the hinge axis 113 are the portions that are closest to the plane P. The first and second proximal portions 122,222 are then sloped away from the plane P in such a way that the most proximal points on the first and second inner surfaces 124,224 are the portions of the inner surfaces 124,224 that are furthest away from the plane P.

The first and second proximal portions 122,222 have first and second gripping surfaces 126,226 respectively. Preferably, the first gripping surface 126 is opposed to the second gripping surface 226 so that during operation the first gripping surface 126 may be squeezed relatively toward the second gripping surface 226. Squeezing the first gripping surface 126 towards the second gripping surface 226 pivots the dilator from a generally insertable position to a generally dilating position.

Preferably, the pivoting dilator 100 is biased in the insertable position using a biasing member, such as a torsion spring 150, shown in FIG. 2. The torsion spring 150 is located between the first proximal end 122 and the hinge axis 113 and pushes the first proximal end 122 and the second proximal end 222 away from each other and the plane P. Torsion spring 150 has an opening 152 therethrough aligned with the passageway between the first and second distal portions 114,214. While FIG. 2 shows a torsion spring 150 as the biasing member, those skilled in the art will recognize that other types of biasing members may be used to bias the dilator 100 in the insertable position. The biasing member may be anything that will squeezably retain the dilator 100 in the insertable position, that does not obstruct the passageway defined by and between the first and second distal portions.

When the first and second proximal ends 122,222 are squeezed together the pivoting dilator 100 pivots into a dilating position, and a cavity is formed along the longitudinal axis 108 that is defined by the first inner surface 124 and the second inner surface 224. Preferably, the cavity is large enough to allow a catheter (not shown) to be inserted into the patient's blood vessel between the first dilator portion 110 and the second dilator portion 210. While the present embodiment shows a first inner surface 124 and a second inner surface 224 having generally semicircular shapes, to accommodate a catheter with a circular cross section, those skilled in the art will recognize that the first and second inner surfaces 124,224 may be shaped to accommodate catheters with many different types of cross-sectional shapes.

Preferably, the dilator 100 is made from a biocompatible rigid or semi-rigid material. Examples of such a material are: titanium, stainless steel, nylon, polyvinylchloride, acrylic, polycarbonate or any other suitable biocompatible rigid or semi-rigid material. Those skilled in the art will recognize that this list of materials is merely exemplary and that there are other suitable materials that may be used to make the dilator 100 without departing from the scope of the present invention.

In use, an incision is made into a patient's skin and then, using the well-known Seldinger technique, an opening is made into the selected vessel. A guidewire (not shown) is then inserted through the incision and into the vessel opening until its distal end is placed at a selected site along the vessel using known imaging techniques. The proximal end of the guidewire protruding from the patient is inserted between the first distal end 114 and the second distal end 214. The pivoting dilator 100, biased in the insertable position, is then slid distally along the guidewire until the distal end 104 of the pivoting dilator 100 is disposed within the patient's vessel and the proximal end 106 of the pivoting dilator remains outside of the vessel.

With the pivoting dilator 100 partially disposed within the vessel, the first proximal end 122 is then squeezed towards the second proximal end 222 pivoting the dilator 100 about hinge axis 113 to the dilating position thereby spreading the first and second distal portions 114,214 away from each other and dilating the vessel. With the dilator 100 in the dilating position and the vessel dilated, the guidewire is removed. Alternatively, the guidewire may be removed prior to squeezing of the first and second proximal ends 122,222 towards each other. Optionally, the guidewire may be left in the vessel until after the catheter is inserted.

The distal tip of the catheter is inserted between the first proximal end 122 and the second proximal end 222. In a situation where the inserting physician has left the guidewire in the vessel, the catheter is inserted over the guidewire; however, if the guidewire has been removed prior to the insertion of the catheter, the catheter may be inserted without the use of a guidewire. With the distal tip of the catheter between the first and second proximal ends 122,222, the catheter is then slid distally, past the first and second proximal portions 114,214 and the first and second hinge portions 112,212 and into the patient's vessel.

Figure 3:
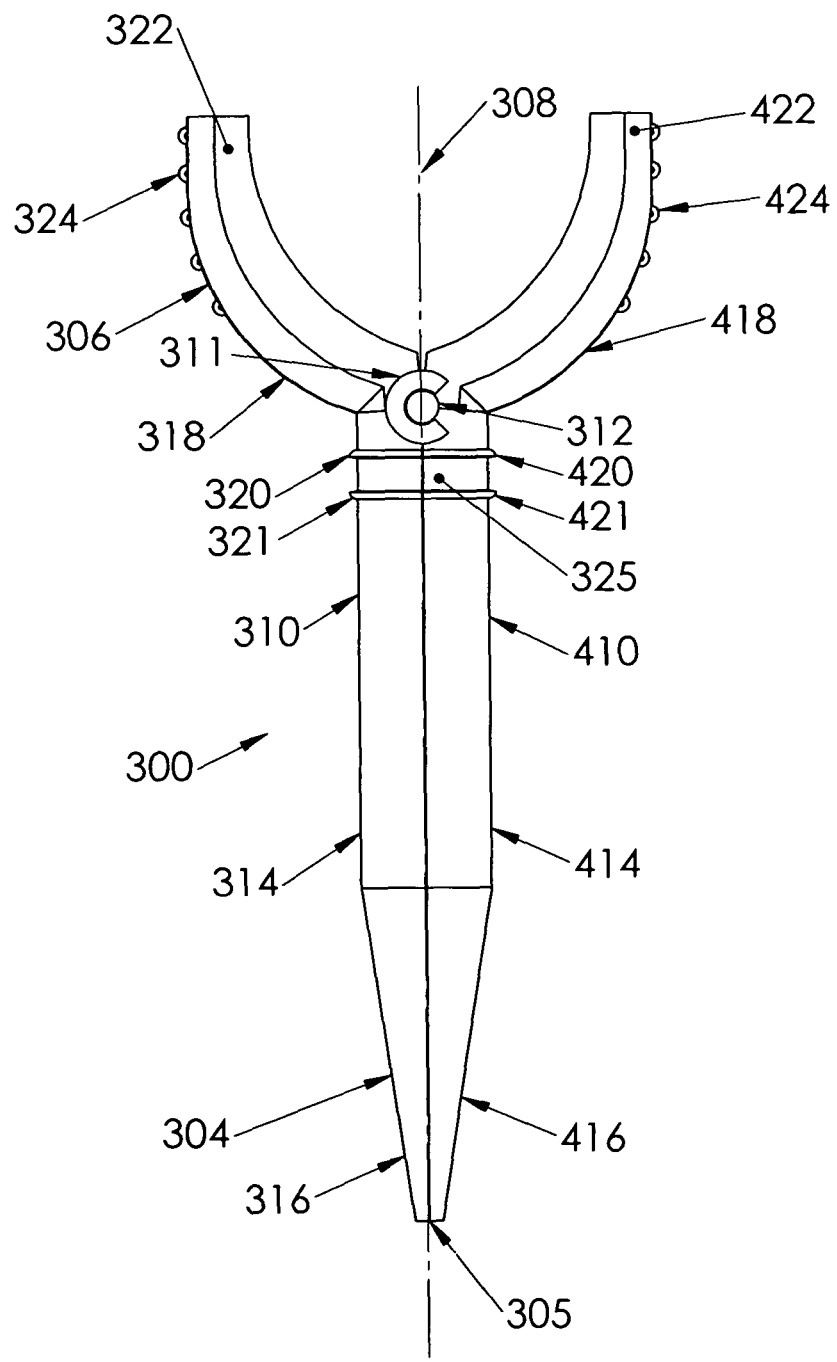
FIG. 3 is a side view of a second embodiment of the pivoting dilator.

A second embodiment of a pivoting dilator 300 is shown in FIG. 3. The dilator 300 has a proximal end 306, a distal end 304 and a longitudinal axis 308 extending therethrough between the proximal end 306 and the distal end 304. The dilator 300 comprises a first dilator portion 310 and a second dilator portion 410. The first dilator portion 310 and the second dilator portion 410 are generally mirror images of each other and are hingedly joined to each other by a hinge pin 311, disposed within a first hinge portion 312 and a second, similar hinge on the opposite side (not shown). Each of the first dilator portion 310 and the second dilator portion 410 have a generally semicircular cross-section, when cut in a plane perpendicular to the longitudinal axis 308. The first dilator portion 310 has a first proximal end 318 and first distal end 314, having a first distal tip 316. The second dilator portion 410 has a second proximal end 418 a second distal end 414, having a second distal tip 416.

The proximal end 306 is generally semi-circular in shape, when viewed from the side, as shown in FIG. 3. The first proximal end 318 and the second proximal end 418 each form approximately one half of the semi-circular shape of the proximal end 306, thereby forming a semi-circular cross-sectioned proximal end 106. The first and second proximal ends 318,418 extend proximally from the hinge pin 311 and away from each other. First and second proximal tip portions 322,422 are located at the proximal-most part of the first and second proximal portions 318,418 and in a direction that is generally parallel to the longitudinal axis 308. A first gripping surface 324 and a second gripping surface 424 are preferably disposed on the first and second proximal portions 318,418 respectively and on the sides of the respective proximal portions 318,418 that are furthest from the longitudinal axis 308 located directly therebetween. The first and second distal tips 316,416 define a distal opening 305 around the longitudinal axis 308 that is sized to allow the dilator 300 to be inserted into a patient's vessel over a guidewire.

It can be seen in FIG. 3 that first and second distal ends 314,414 are elongated compared to those of distal portions 116,216 of FIGS. 1 and 2. A first proximal retaining rib 320 and a first distal retaining rib 321 are located on the first dilator portion 310, preferably located just distally of the hinge pin 311 and closer to the hinge pin 311 than the first distal tip 316. A second proximal retaining rib 420 and a second distal retaining rib 421 are located on the second dilator portion 410 just distally of the hinge pin 311 and closer to the hinge pin 311 than the second distal tip 416. The proximal and distal retaining ribs 320,420;321,421 are aligned with each other in order to form retaining ribs that completely encircle the dilator 306. A biasing member, such as a rubber band 325, is disposed around the dilator 300 and retained proximally of the distal retaining rings 321,421 and distally of the proximal retaining rings 320,420. The rubber band 325 biases the dilator in the closed, or insertable, position. With the biasing member spaced substantially from the distal tip 305, the distal end 304 is openable when a catheter is inserted into and through dilator 300. Optionally, operation of the dilator 300 may be similar to the operation of the dilator 100.

A third embodiment of a dilator 500 is shown in FIGS. 4 and 5. Like the previous embodiments disclosed herein, the dilator 500 of FIG. 4 comprise first and second dilator portions 510,610 that preferably are identical to each other. The dilator 500 comprises a proximal end 506, a distal end 504 and a longitudinal axis 508 extending therethrough between the proximal end 506 and the distal end 504. In use, the distal end 504 is inserted into the venotomy to be dilated (not shown) and the proximal end 506 remains outside of the vessel.

The first dilator portion 510 comprises a first distal portion 514 located at the distal end 504 of the dilator 500, a first proximal portion 522 disposed at the proximal end 506 of the dilator 500 and a first hinge portion 512 disposed between the first distal portion 514 and the first proximal portion 522. As shown best in FIG. 5, the first hinge portion 512 includes a first male hinge portion 512a and a first female hinge portion 512b. Referring back to FIGS. 4 and 5, the second dilator portion 610 comprises a second distal portion 614 located at the at the distal end 504 of the dilator 500, a second proximal portion 622 disposed at the proximal end 506 of the dilator 500 and a second hinge portion 612 disposed between the second distal portion 614 and the second proximal portion 622.

Like the other embodiments described herein, as shown best in FIG. 5, each of the first dilator portion 510 and the second dilator 610 portion have a generally "C" shaped cross-section, when the cross-sectional view is taken in a plane that is perpendicular to the longitudinal axis 508. Combined, the first and second dilator portions 510,610 form a dilator 500 having a generally circular cross section. The first and second dilator portions 510,610 define a generally circular passageway, extending therethrough along the longitudinal axis 508.

FIG. 5 shows the first dilator portion 510, which is one half of the pivoting dilator assembly 500 and is identical to the second dilator portion 610 of FIG. 4. The first male hinge portion 512a is generally circular in shape and is centered about a hinge axis 513. The first female hinge portion 512b is generally "C" shaped and is also centered about the hinge axis 513. The first female hinge portion 512b is sized to hingedly engage a second male hinge portion (not shown) of the second dilator portion 610, which is identical to the first male hinge portion 512a of the first dilator portion 510. Likewise, the first male hinge portion 512a is sized to hingedly engage a second female hinge portion (not shown) of the second dilator portion 610, which is identical to the first female hinge portion 512b of the first dilator portion 510.

Each of the first and second proximal portions 522,622 respectively extend in a generally proximal direction from the first and second distal portions 514,614 and at an angle β from the longitudinal axis 508, shown in FIG. 4 as being about 5 degrees. Preferably, the first and second proximal portions 522,622 and the first and second distal portions 514,614 meet, respectively, at a point proximate to the first and second hinge portions 512,612 respectively. The dilator may also have a biasing member adapted to bias the dilator in the inserting position, such as the biasing members 150 and 325 shown in FIGS. 2 and 3, respectively. As shown in FIG. 4, biasing member 525 may be a rubber band that biases together the distal portions 514,614 when in the closed position, where first and second retaining ribs 520,521; 620,621 are sized to retain biasing member 525 therebetween at a location just distal of the hinge portions 512,612. The first and second proximal retaining ribs 520,620 and the first and second distal retaining ribs 521,621 mate to form retaining ribs that completely encircle the dilator 500 when the dilator 500 is disposed in the insertable position.

A first handle 530 is disposed on the first proximal portion 522 and is generally circular in shape and sized to accommodate the inserting practitioner's finger or thumb during use of the dilator 500. Preferably, a part of the first handle 530 is fixedly connected to the first proximal portion 522 and a first support bar 532 joined to first handle 530 extends to a point on the first dilator portion 510 located between the first proximal portion and the first hinge portion 512, but may extend to any point on the first dilator portion 510. The support bar 532 is preferably fixedly connected to both the first dilator portion 510 and the first handle 530 and may also be sized to eliminate any space between the first support bar 532, the first proximal portion 522 and the first handle 530. A second handle 630 is disposed on the second proximal portion 622. Preferably, the second handle 630 is identical to first handle 530, with a second support bar 632 extending to a point on the second dilator portion 610, located between the second proximal portion 622 and the second hinge portion 612, but may extend from the second handle 630 to any point on the second dilator portion 610. The support bar 632 is preferably fixedly connected to both the second dilator portion 610 and the second handle 630 and similarly may also be sized to eliminate any space between the second support bar 632, the second proximal portion 622 and the second handle 630. Those skilled in the art will recognize that other handle configurations may be utilized to facilitate the operation of the dilator 500. Those skilled in the art will also recognize that each of the first dilator portion 510 and the second dilator portion 610 may each be of unitary construction or constructed as an assembly.

Optionally, the first proximal portions 522,622 of the proximal ends 506,606 of the two portions 510,610 may be oriented at a wider angle β where β is about 45 degrees, for the convenience of the practitioner, but the angle could be up to 50 degrees or so or less than 45 degrees. Providing the two dilator proximal ends 506,606 initially at such an angle provides a clearance for insertion of the catheter itself into the passageway between the distal ends 514,614 and through the distal tip 504 of the dilator which will then force open the distal ends 514,614 upon frictional engagement with the inner surfaces thereof adjacent the distal dilator tip 504, with the handle defined by proximal ends 506,606 being a means to steady the dilator.

A fourth embodiment is disclosed in FIGS. 6 to 23, of dilator assembly 700. Dilator 700 is made of several components: first and second proximal or handle portions 702,704; first and second distal portions 706,708 defining a longitudinal passageway 710 therethrough; and first and second hub sections 712,714 (shown as integral with distal portions 706, 708, respectively) to which the proximal and distal portions are joined. FIG. 6 is an isometric view of dilator assembly 700, shown in its pivoted-open position; FIG. 7 is an enlarged isometric view of the hub connection; FIGS. 8 and 9 are top and side views of the dilator assembly 700.

First and second proximal or handle portions 702,704 are mirror images of each other, and first handle portion 702 is shown in an isometric view (FIG. 10), a top view (FIG. 11), a side view (FIG. 12) and an end view (FIG. 13). FIGS. 11 to 13 illustrate the complex angle of the proximal end portion 716 with respect to the distal end portion 718 of first handle portion 702. Similarly angled is proximal end portion 720 from distal end portion 722 of second handle portion 704. Angle γ in FIG. 11 may be about 16 degrees; angle δ in FIG. 12 may be about 27 degrees; and the angle ε in FIG. 13 may be about 30 degrees, as is illustrated. Extending from the distal portions 718,722 are connection sections 724,726 of first and second handle portions 702,704 each containing a pair of bores therethrough through which screws 730 will extend to join handle portions 702,704 to respective first and second hub sections 712,714, by being threaded into aligned bores 732 (see FIGS. 15 to 22) thereof.

First and second hub sections 712,714 are joined at a hinge 734, and are pivotable with respect to hinge 734 within a limited range, such as about ten degrees, by manipulation of first and second handles 702,704, opening and closing first and second distal portions 706,708 and their passageway portions 710a, 710b.

Referring now to FIGS. 14 and 19, first and second distal portions 706,708 are seen in isometric views to include elongated first and second semi-cylindrical sections 736,738 and tapered first and second distal end sections 740,742 that extend to respective first and second distal tips 744,746 that together form a distal tip 750 of the dilator device 700 when in the closed position, as shown in FIGS. 8 and 9. Distal tip 750 preferably defines an aperture that may be as small as 0.046 inches (1.17 mm), but it could be smaller depending on the gauge of the guide wire to be used, needing only be large enough to accommodate the diameter of a guide wire extending therethrough. When the dilator assembly 700 is pivoted to its open position, the lateral opening between the respective distal tips 744,746 may be as large as about 0.200 to 0.300 inches (5.1 to 7.6 mm). Further details of distal portions 706,708 are seen in top and side views FIGS. 15, 16, 20 and 21, end views FIGS. 17 and 22 and enlarged hub views FIGS. 18 and 23.

First and second hub sections 712,714 are seen, in FIGS. 14 to 23, to have side walls 752,754 that surround and define the proximal end of passageway 710. Beveled interior surfaces 764 of proximal ends 756,758 diverge to define a lead-in to facilitate insertion thereinto of the distal tip of a catheter assembly into passageway 710, and the beveled surfaces may be each at a respective angle of about 5 degrees from axial. The proximal ends 756,758 of the side walls also define the pivoting mechanism. As shown in the Figures, the pivoting mechanism comprises two portions aligned with each other on opposing sides of the passageway 710 to define a pivot axis transverse to the passageway 710. On each side a pivot portion comprises a cylindrical embossment 760 (see FIG. 18) that is rotatably received within a substantially circumferential seat 762 (see FIG. 23); the two cylindrical embossments 760 are integral portions of hub section 714, projecting from side walls 754, while the two seats 762 are integrally defined into the side walls 752 of hub section 712. As shown in FIGS. 18 and 23, beveled surfaces 766 of proximal ends 756 of side walls 752 are at an angle of about 5 degrees and will abut beveled surfaces 768, also at an angle of about 5 degrees, of proximal ends 758 of side walls 754 when the dilator assembly 700 is pivoted into its open position, so that the abutting beveled surfaces could serve as a stop to limit the size of opening.

With reference now to FIGS. 7, 14 and 19, it may be seen that the passageway 710 extending along first and second distal portions 706,708 is oval/rectangular in cross-section, thus being able to accommodate catheters that are round having a diameter about equal to the narrower dimension, but also being able to accommodate double catheters such as the SCHON-CATH® catheter sold by AngioDynamics, Queensbury, N.Y. . The distal tip can be opened to a width selected by the practitioner to be sufficient for the catheter to extend therepast through the venotomy and into the vasculature of the patient.

It is preferable in the embodiment of dilator assembly 700 for at least the handles to be of rigid material such as stainless steel. The stainless steel could also be used for the distal portions. Other materials that may be useful include nylon 6/6, of which the hub sections could be made, in which cases the screws 760 could be rivets. An option with this embodiment is that the handles and hub sections could be sterilized for re-use, with an array of different sizes of dilator portions that range in size for use with catheters of varying diameters.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed:

1. A pivoting dilator comprising:
opposed first and second dilator portions hingedly intereconnected to one another with a longitudinal axis extending longitudinally between the first and second dilator portions, each dilator portion extending longitudinally between a proximal end and a distal end, with each distal end defining a tapered tip, each tapered tip tapering from a proximal tip location to a distal tip location with a longitudinal length between the proximal tip location and the distal tip location being greater than a diameter of the opposed first and second dilator portions at the proximal tip location, the first and second dilator portions pivotal between an insertion position wherein the tapered tips are proximate one another such that an enclosed passageway is defined between at least the opposed distal ends with an opening through the tapered tips and a dilating position wherein the tapered tips are spaced from one another; and
a gripping surface extending from each dilator portion proximal end, each gripping surface configured such that the gripping surface moves toward the longitudinal axis as the first and second dilator portions are moved from the insertion position to the dilating position
wherein an inside surface of each tapered tip defines a contact surface configured such that upon receipt of a force in the longitudinal direction, the first and second dilator portions pivot toward the dilating position.

2. The pivoting dilator according to claim 1, wherein the first and second dilator portions include complementary hinge components.

3. The pivoting dilator according to claim 2, wherein the complementary hinge components include at least one male portion fitted laterally into a C-shaped female portion.

4. The pivoting dilator according to claim 1, wherein the first dilator portion and the second dilator portion are identical.

5. The pivoting dilator according to claim 1, wherein the proximal end of the first dilator portion is biased away from the proximal end of the second dilator portion by a biasing element engaged with the first and second dilator portions and configured to provide access to the passageway.

6. The pivoting dilator according to claim 1, wherein in the insertion position, the proximal end of each of the first and second dilator portions extends in a respective plane non-parallel relative to the longitundinal axis.

7. The pivoting dilator according to claim 6, wherein each of the planes is at an angle of about 5 degrees relative to the longitudinal axis.

8. The pivoting dilator according to claim 6, wherein each of the planes is at an angle relative to the longitudinal axis from about 5 degrees to about 50 degrees.

9. The pivoting dilator according to claim 6, wherein each of the planes is at an angle of about 45 degrees relative to the longitudinal axis.

10. The pivoting dilator according to claim 1, wherein the gripping surfaces are defined along first and second handles discrete from and affixed to respective first and second hub sections of the first and second distal portions.

11. The pivoting dilator according to claim 10, wherein the first and second hub sections are joined to each other by a hinge.

12. The pivoting dilator according to claim 11, wherein the hinge comprises at least one male hinge section on one of the first and second hub sections, and at least one complementary female hinge section on the other of the first and second hub sections.

13. The pivoting dilator according to claim 12, wherein the hinge comprises two male hinge sections on the one of the first and second hub sections, and two complementary female hinge sections on the other of the first and second hub sections.

14. The pivoting dilator according to claim 13, wherein the two male hinge sections are disposed on first opposing walls of the one of the first and second hub sections at a proximal end thereof, and the two female hinge sections are disposed on second opposing walls of the other of the first and second hub sections at a proximal end thereof, wherein the first and second opposing walls define therebetween a proximal entrance to the passageway.

15. A pivoting dilator comprising:
opposed first and second dilator portions hingedly intereconnected to one another with a longitudinal axis extending longitudinally between the first and second dilator portions, each dilator portion extending longitudinally between a proximal end and a distal end, with each distal end defining a tapered tip, each tapered tip tapering from a proximal tip location to a distal tip location with a longitudinal length between the proximal tip location and the distal tip location being greater than a diameter of the opposed first and second dilator portions at the proximal tip location, the first and second dilator portions pivotal between an insertion position wherein the tapered tips are proximate one another such that an enclosed passageway is defined between at least the opposed distal ends with an opening through the tapered tips and a dilating position wherein the tapered tips are spaced from one another; and
a gripping surface extending from each dilator portion proximal end, each gripping surface configured such that the gripping surface moves toward the longitudinal axis as the first and second dilator portions are moved from the insertion position to the dilating position
wherein in the insertion position, a diameter of the passageway through the tapered tips is less than half the diameter of the passageway at the proximal tip location.

16. The pivoting dilator according to claim 15, wherein the first and second dilator portions include complementary hinge components.

17. The pivoting dilator according to claim 16, wherein the complementary hinge components include at least one male portion fitted laterally into a C-shaped female portion.

18. The pivoting dilator according to claim 15, wherein the proximal end of the first dilator portion is biased away from the proximal end of the second dilator portion by a biasing element engaged with the first and second dilator portions and configured to provide access to the passageway.

19. The pivoting dilator according to claim 15, wherein in the insertion position, the proximal end of each of the first and second dilator portions extends in a respective plane non-parallel relative to the longitundinal axis.

20. The pivoting dilator according to claim 15, wherein the proximal end of the first dilator portion is biased away from the proximal end of the second dilator portion by a biasing element engaged with the first and second dilator portions and configured to provide access to the passageway.

21. The pivoting dilator according to claim 15, wherein in the insertion position, the proximal end of each of the first and second dilator portions extends in a respective plane non-parallel relative to the longitundinal axis.

22. A pivoting dilator comprising:
- opposed first and second dilator portions hingedly interconnected to one another with a longitudinal axis extending longitudinally between the first and second dilator portions, each dilator portion extending longitudinally between a proximal end and a distal end, with each distal end defining a tapered tip, each tapered tip tapering from a proximal tip location to a distal tip location with a longitudinal length between the proximal tip location and the distal tip location being greater than a diameter of the opposed first and second dilator portions at the proximal tip location, the first and second dilator portions pivotal between an insertion position wherein the tapered tips are proximate one another such that an enclosed passageway is defined between at least the opposed distal ends with an opening through the tapered tips and a dilating position wherein each tapered tip is spaced from the longitudinal axis and the tapered tips are spaced from one another; and
- a gripping surface extending from each dilator portion proximal end, each gripping surface configured such that the gripping surface moves toward the longitudinal axis as the first and second dilator portions are moved from the insertion position to the dilating position, each gripping surface spaced from the longitudinal axis in the insertion position a distance greater than the respective tapered tip is spaced from the longitudinal axis in the dilating position,
- wherein an inside surface of each tapered tip defines a contact surface configured such that upon receipt of a force in the longitudinal direction, the first and second dilator portions pivot toward the dilating position.

23. The pivoting dilator according to claim 22, wherein the first and second dilator portions include complementary hinge components.

24. The pivoting dilator according to claim 22, wherein the gripping surfaces are defined along first and second handles discrete from and affixed to respective first and second hub sections of the first and second distal portions.

25. The pivoting dilator according to claim 24, wherein the first and second hub sections are joined to each other by a hinge.

26. A pivoting dilator comprising:
- opposed first and second dilator portions hingedly interconnected to one another with a longitudinal axis extending longitudinally between the first and second dilator portions, each dilator portion extending longitudinally between a proximal end and a distal end, with each distal end defining a tapered tip, each tapered tip tapering from a proximal tip location to a distal tip location with a longitudinal length between the proximal tip location and the distal tip location being greater than a diameter of the opposed first and second dilator portions at the proximal tip location, the first and second dilator portions pivotal between an insertion position wherein the tapered tips are proximate one another such that an enclosed passageway is defined between at least the opposed distal ends with an opening through the tapered tips and a dilating position wherein each tapered tip is spaced from the longitudinal axis and the tapered tips are spaced from one another; and
- a gripping surface extending from each dilator portion proximal end, each gripping surface configured such that the gripping surface moves toward the longitudinal axis as the first and second dilator portions are moved from the insertion position to the dilating position, each gripping surface spaced from the longitudinal axis in the insertion position a distance greater than the respective tapered tip is spaced from the longitudinal axis in the dilating position,
- wherein in the insertion position, a diameter of the passageway through the tapered tips is less than half the diameter of the passageway at the proximal tip location.

* * * * *